United States Patent

Barker

[11] Patent Number: 5,947,967
[45] Date of Patent: Sep. 7, 1999

[54] VARIABLE ANGLE CONNECTOR

[75] Inventor: B. Thomas Barker, Memphis, Tenn.

[73] Assignee: SDGT Holdings, Inc., Wilmington, Del.

[21] Appl. No.: 08/955,731

[22] Filed: Oct. 22, 1997

[51] Int. Cl.$^6$ .................................................. A61B 17/56
[52] U.S. Cl. ................................ 606/61; 606/60; 606/72; 606/73; 606/62
[58] Field of Search ................................ 606/61, 60, 72, 606/73, 62

[56] References Cited

U.S. PATENT DOCUMENTS

| | | |
|---|---|---|
| 5,129,900 | 7/1992 | Asher et al. . |
| 5,261,909 | 11/1993 | Sutterlin et al. . |
| 5,425,732 | 6/1995 | Ulrich . |
| 5,487,744 | 1/1996 | Howland . |
| 5,498,264 | 3/1996 | Schlapfer et al. . |
| 5,501,684 | 3/1996 | Schlapfer et al. . |
| 5,527,314 | 6/1996 | Brumfield et al. . |
| 5,562,661 | 10/1996 | Yoshimi et al. . |
| 5,584,831 | 12/1996 | McKay . |
| 5,611,800 | 3/1997 | Davis et al. . |
| 5,643,263 | 7/1997 | Simonson . |

Primary Examiner—Michael Buiz
Assistant Examiner—Tan-Uyen T. Ho
Attorney, Agent, or Firm—Woodard, Emhardt, Naughton, Moriarty & McNett

[57] ABSTRACT

A connector for connecting a bone screw to a spinal rod includes a body defining first and second channels for receiving the screw and rod, respectively. The body includes a tapered outer surface adjacent the channel receiving the bone screw. An internally tapered washer fits over the tapered outer surface of the body and is rotatable about the surface. The washer includes a slot to receive the bone screw. The screw channel in the body includes diverging walls so the bone screw can adopt variable angular orientations relative to the rod. The tapered washer can lock the screw in position by frictional engagement with the tapered outer surface of the body. A set screw operates as a pressure member to compress the rod, screw and body and washer together. In one embodiment, the rod and screw are in direct contact. In another embodiment, a third channel extends between the first and second channels to receive a transfer pin therein to provide indirect engagement of the rod and screw.

30 Claims, 6 Drawing Sheets

VARIABLE ANGLE CONNECTOR

BACKGROUND OF THE INVENTION

The present invention relates generally to the field of spinal implant systems, and particularly systems of the type that employ vertebral fixation elements engaged to elongated members spanning the spine. More particularly, the invention concerns a connector that provides variable angle adjustability between the bone fixation element and the elongated member.

Several systems have been developed for the use in correcting and stabilizing spinal deformities and facilitating spinal fusion. In one such system, an elongated member, typically in the form of a bendable rod, is longitudinally disposed adjacent the vertebral column and is fixed to various vertebrae along the length of the column by way of a number of fixation elements. A variety of fixation elements are used, such as hooks, bone bolts and screws, each configured to engage a specific portion of a vertebra.

An example of a spinal fixation system of this type is the TSRH® Spinal System of Sofamor Danek Group, Inc. In this product, spinal hooks and bone screws are engaged to a spinal rod by way of eyebolts. The eyebolts and associated clamping nut provide a three-point shear clamp that positively locks the hook or screw element to the spinal fixation rod.

In its early years, the TSRH® Spinal System only permitted fixed orientations of the spinal hook or bone screws with respect to the rod. In other words, the angle and attitude between the fixation element and spinal rod could not be varied. In order to address this limitation, the TSRH® variable angle screw was developed. The details of this screw are described in U.S. Pat. No. 5,261,909, owned by the Assignee of the present invention. In general terms, this variable angle screw utilized a separate washer that was engaged over a clamping eyebolt. The washer and a face of the head of the fixation element included interdigitating splines that permitted variable angular orientations between the fixation element and the washer. A nut is used to clamp the assembly together, thereby fixing the specific angular relationship between the bone engaging fastener and the spinal rod. While this variable angle screw revolutionized spinal fixation, and particularly rod-based systems, it too has certain limitations. For instance, the angular orientations that can be accomplished are limited to the number and arrangement of interdigitating splines. In other words, the TSRH® variable angle screw, as with the variable angle screws developed subsequently, are limited to a finite number of angular positions within the range of motion. These finite angular positions have, at times, caused surgeons to be forced to manipulate either the vertebra and/or the implants in order to properly mate the fixation element to the variable angle connector engaged to the spinal rod.

Another limitation of the original TSRH® variable angle screw is that it does not accommodate variable height positions along the axis of the screw. In other words, the distance between the spinal rod and the vertebral body cannot be varied mechanically, but can only be varied by increasing or decreasing the depth that the screw is threaded into the vertebral body. In the case of spinal hooks, this latter capability is not present.

Contemporaneous with the variable angle screw, Sofamor Danek, developed the GDLH® Spinal Fixation System. This GDLH® System includes spinal fixation elements, such as pedicle hooks, that incorporate an elongated stem. The GDLH® System also includes a rod connector that receives the elongated stem and permits variable height or axial positions of the fixation element relative to the connector and the spinal rod. In this system, the portion of the elongated shank of the fastener extending beyond the connector can be severed to reduce the overall profile of the construct. While the GDLH® System addresses the difficulty of height variability, the system does not include a variable angle capability.

Thus far, there is no known spinal system that provides a reliable connection between a fixation element and an elongated member spanning the spine, while permitting variable angular and height, or axial, orientations between the two elements. Likewise, there is no known system that combines these degrees of freedom of relative movement in an infinitely variable fashion. Such a system would significantly eliminate the problem of "fiddle factor" in which a surgeon must manipulate either the spine or the instrumentation in order to complete the construct.

SUMMARY OF INVENTION

In view of these limitations of prior art devices, the present invention contemplates a connector for connecting a bone engaging fastener to a longitudinal member that substantially eliminates the "fiddle factor" of prior art devices. The inventive connector is configured for engaging a bone engaging fastener, having an elongated shank, to an elongated longitudinal member. In the preferred embodiment, the fastener is a bone screw, such as a Schantz-type screw, and the longitudinal member is a spinal rod.

In one aspect of the invention, the connector includes a body that defines a first channel configured for receiving a portion of the longitudinal member, or rod, and a second channel adjacent the first channel that is configured for receiving the elongated shank of the fastener. In one embodiment, the first and second channels intersect to define a window therebetween that permits direct contact between the elongated shank and the longitudinal member. In another embodiment, a third channel is defined that communicates between the first and second channels, so that direct contact between the shank of the fastener and the longitudinal member is not permitted.

In accordance with the invention, the first channel is elongated so that the longitudinal rod can assume various positions along the length of the channel. In another aspect of the invention, the second channel that receives the elongated shank of the fastener is configured to permit variable angular orientations of the fastener with respect to the body of the connector, and ultimately with respect to the longitudinal member. In one embodiment, the second channel includes at least a pair of outwardly diverging walls. Preferably, the second channel includes one pair of outwardly diverging walls originating generally at the center of the body and projecting upward, and a second pair of walls originating at the center of the body and projecting downward, so that in cross-section the channel gives the appearance of a bowtie. In this configuration, the elongated shank of the bone engaging fastener can be pivoted about the center of the body and assume infinitely variable angular orientations between the outwardly diverging angled walls.

A central element of the invention is a washer that is received about the outside of the connector body. The washer defines a slot at one end that is configured to receive, in one embodiment, the elongated shank of the fastener. In accordance with one aspect of the invention, the washer and the outside of the connector body include complementary circumferentially tapered or frusto-conical surfaces. The washer is slidably seated at one end of the body and arranged so that as it slides over the outer conical surface of the body an increasing frictional engagement between the washer and the body is generated. Prior to such motion, the washer can be freely rotated about the body to accommodate variable angular positioning of the shank of the bone engaging fastener with respect to the connector body. Once the angular position of the fastener is established, the washer can be translated along the connector body until a tight frictional engagement is achieved between the inner surface of the washer and the outer surface of the body. The angles of the outer surface and the inner surface can form self-locking or self-holding tapers, or can be self-releasing tapers.

In still another feature of the inventive connector, a pressure member is provided that acts upon either the shank of the bone engaging fastener or the longitudinal member, depending upon which component is engaged by the washer. In the preferred embodiment, the washer engages the elongated shank of the fastener, so the pressure member operates on the longitudinal member. In accordance with one embodiment of the invention, the connector body includes a threaded bore communicating with the first channel. The bore is arranged so that a pressure member, such as a set screw, is threaded into the channel to press the longitudinal member toward the elongated shank of the bone engaging fastener. In one embodiment, the direct contact between the rod and the shank of the fastener causes the fastener to translate toward one end of the body as the pressure member operates on the spinal rod. At the same time, then, the elongated shank of the fastener pushes the washer in the same direction. This movement of the washer causes it to lock in frictional engagement, as described above. Fully tightening the set screw into the body and against the spinal rod achieves final and firm engagement between all of the components of the connector assembly of the present invention.

In a variation of the invention, a transfer member is slidably disposed within the third channel oriented between the two channels in the body. The transfer member transfers the load exerted against the spinal rod indirectly to the shank of the bone engaging fastener. This transfer member is useful where a lateral offset between the spinal rod and the bone engaging fastener is desired. In one specific embodiment, the transfer member is in form of a cylindrical plug with annular circumferential ridges formed at the opposite ends of the plug for engagement and/or penetration of the respective shank of the fastener and longitudinal member.

It is one object of the present invention to provide a connector assembly for connecting a bone engaging fastener to a longitudinal member adjacent the spinal column of a patient. One particular object is achieved by features of the invention that permit infinitely variable relative angular and height positioning of the fastener and the longitudinal member.

Another object of the invention is to provide a connector assembly which can firmly lock the relative rotational position of the fastener to the longitudinal member, while still permitting variations in axial or height orientation. Other objects and particular benefits of the present can be discerned from the following text and accompanying Figures illustrating certain embodiments of the invention.

DESCRIPTION OF THE PREFERRED EMBODIMENTS

Figure 1:
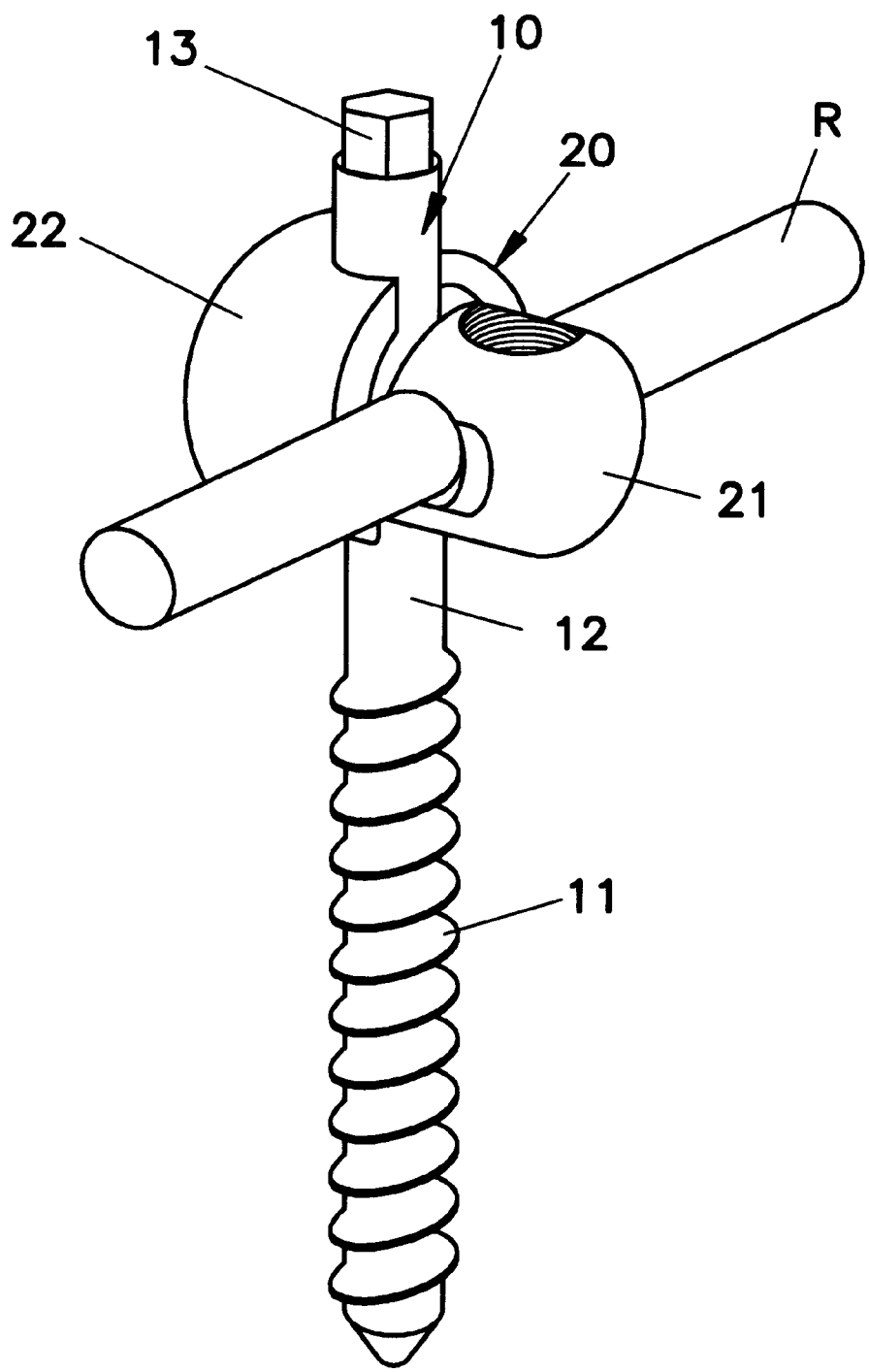
FIG. 1 is a perspective view of a connector assembly in accordance with the present invention connecting a bone engaging fastener to an elongated spinal rod.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention contemplates a connector assembly for connecting a bone engaging fastener to a longitudinal member. In the preferred embodiment, the bone engaging fastener is a bone screw, particularly a Schantz-type bone screw. However, it is contemplated that other types of fasteners can be engaged by the present inventive connector assembly. For example, the fastener could constitute a vertebral hook. Similarly, the preferred embodiment of the invention contemplates that the longitudinal member is an elongated spinal rod, such as the rod used with the TSRH® Spinal System of Sofamor Danek Group. However, other forms of longitudinal members are contemplated, provided that the members are configured for spanning a portion of the spinal column of a patient. For example, the longitudinal member could constitute a bar or a portion of a spinal plate.

The connector assembly according to the illustrated embodiments permits connection of the bone engaging fastener to the longitudinal member at infinitely variable angular orientations and infinitely variable axial or height orientations. Reference to variable angular orientations means that the longitudinal axes of the bone engaging fastener, for example, can be rotated or pivoted in a plane that is perpendicular to the plane passing through the longitudinal axes of the longitudinal member, or rod. For example, in a typical rod-screw instrumentation of the spine, the rod extends along the length of the spine with the screw extending anteriorly into a portion of a vertebra. The relative angular orientation is then substantially in the sagittal plane of the spine. Variable axial or height adjustment is intended to accommodate different locations of the longitudinal member relative to the underlying vertebra. For instance, in some instances, it is not possible to contour the rod sufficiently so that the rod is always the same distance posteriorly from each of the instrumented vertebrae. Adjustment in axial position or height allows the connector to accommodate this dimensional variation and still interconnect the bone engaging fastener to the longitudinal member.

Figure 8:
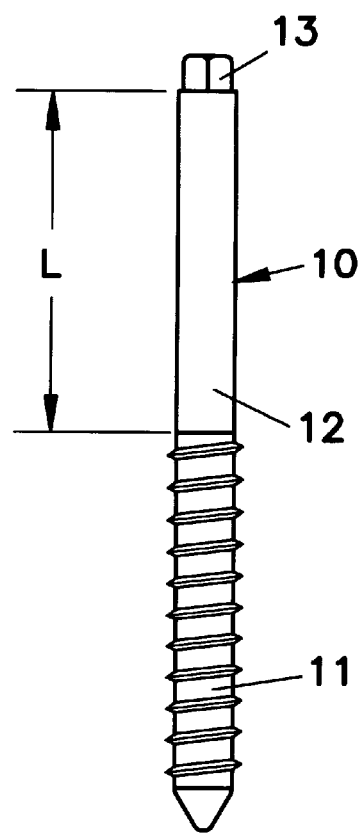
FIG. 8 is a side elevational view of a bone engaging fastener engaged by the connector assembly shown in FIG. 1.

In accordance with one embodiment of the present invention, a connector assembly 20 engages a bone engaging fastener 10 to a spinal rod R. As indicated above, the bone engaging fastener can be of a variety of forms, including a hook or a screw. However, for the purposes of the preferred embodiment, and for simplicity in illustrating the concepts of the invention, the bone engaging fastener 10 is a bone screw (see also FIG. 8). In a specific preferred embodiment, the bone screw is a Schantz-type screw which includes lower bone engaging threads 11 and a smooth elongated shank 12 at the upper portion of the screw. A hex drive portion 13 is formed at the end of the smooth shank for engagement by a driving tool to thread the bone screw 10 into a vertebra. Preferably, the elongated shank 12 is smooth and circular in cross-section; however, the connector assembly of the present invention can be applicable to bone screws having other configurations for the shank 12. For example, the shank 12 could include some surface pattern, such as knurling. Similarly, while a circular cross-section is preferred, the shank 12 could have a square or multi-sided non-circular cross-section. The connector assembly of the present invention is also adapted to mate with a variety of configurations of spinal rod R. For example, the rod could be smooth or could include surface features or roughness. In addition, although the rod is preferably circular in cross-section, it could also have a non-circular cross-section.

Figure 2:
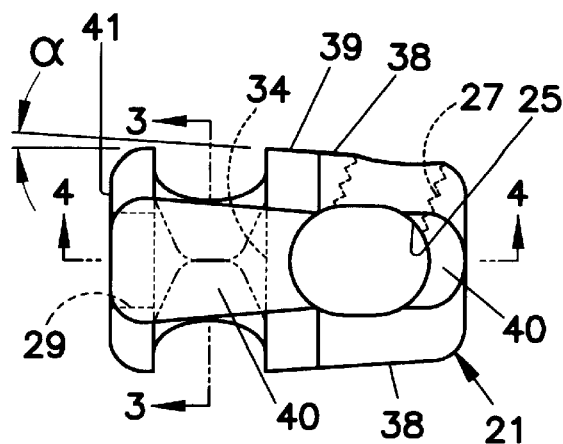
FIG. 2 is a side elevational view of the connector body forming part of the connector assembly shown in FIG. 1.

The connector assembly 20 as shown in FIG. 1 includes a tapered body 21 and a tapered washer 22 that mates with the body 21. Details of the tapered body 21 can be seen with reference to FIGS. 2–4. In the preferred embodiment, the tapered body includes an elongated rod slot 25. The slot preferably includes a radius at its ends separated by a linear section. The slot 25 is elongated so that the rod R disposed within the slot can translate along the length of the slot. A threaded bore 27 opens at the outer surface of the body and extends to the elongated slot 25 adjacent one end. The threaded bore 27 is oriented at an angle so that a pressure member extending through the bore applies a force against the spinal rod R disposed within the slot 25 to push the rod toward the opposite end of the slot 25. In the preferred embodiment, one threaded bore 27 is provided. However, a second bore can be included at the opposite side of the body 21 so that the body of the connector assembly 20 can be placed on the rod in any orientation. As depicted in FIG. 1, when the tapered body 21 is properly oriented, the threaded bore 27 is facing outward from the patient so that the set screw can be engaged in a top-loading and top-tightening fashion.

In one embodiment, the tapered body 21 further defines a central bore 29 extending from end 41 to the rod slot 25. The central bore 29 intersects the rod slot at a window 31. The central bore 29 is sized to receive a transfer pin, which is described in more detail herein. The central bore 29 can also include a threaded portion 30 adjacent the end 41. The threaded portion 30 can be used for receiving an insertion or stabilizing tool. Alternatively, the transfer pin to be described herein can be externally threaded so that it can be advanced into the central bore 29 by threading through the threaded portion 30 and into the non-threaded central bore 29.

In a further feature of the invention, the tapered body 21 defines a screw channel 34. In the preferred embodiment, the screw channel 34 is oriented perpendicular to the elongated rod slot 25. In the embodiment of the tapered body 21 shown in FIGS. 2–4, the screw channel 34 is laterally offset from the rod slot 25 toward the end 41 of the tapered body 21. The screw channel 34 also intersects the central bore 29, as depicted in FIG. 4. Consequently, the central bore 29 provides the only communication between the elongated rod slot 25 and the screw channel 34 in this embodiment.

Figure 3:
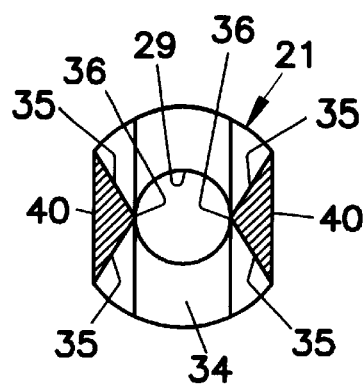
FIG. 3 is an end cross-sectional view of the connector body shown in FIG. 2 taken along line 3—3 as viewed in the direction of the arrows.
Figure 4:
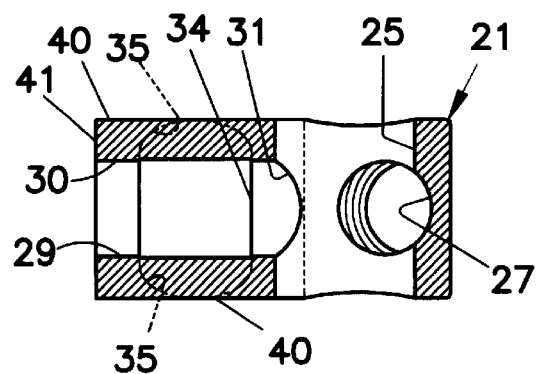
FIG. 4 is a side cross-sectional view of the connector body shown in FIG. 2 taken along line 4—4 as viewed in the direction of the arrows.

In order to achieve the multi-angle capabilities of the connector assembly 20, the screw channel 34 includes a number of angled walls 35, which can be seen most clearly in FIG. 3. In the preferred embodiment, the screw channel 34 is defined by two sets of opposite angled walls 35. Both sets of angled walls 35 diverge from a pair of central vertices 36 that are aligned along the central axis of the central bore 29 and the tapered body 21. In other words, the angled walls 35 of the screw channel 34 diverge outwardly from a central vertex 36 on opposite sides of the screw channel 34. A bone screw disposed within the screw channel 34 can then be oriented at any angle between the walls 35 of the screw channel 34. Moreover, the screw channel 34 is elongated along the axis of the tapered body 21. This permits the bone screw 10 to translate axially along the length of the tapered body 21 so that the lateral distance between a rod R within the rod slot 25 and the bone screw can be varied.

In the preferred embodiment, the screw channel 34 assumes a "bowtie" shape as the angled walls 35 diverge from the central vertices 36. However, the present invention contemplates other arrangements of angled walls 35 within the screw channel 34. For instance, one of the angled walls 35 at the upper portion of the tapered body 21 can be set at a different angle than the angle of the opposite wall. In the preferred embodiment, the bone screw can sweep through equal angles in either direction from a vertical line passing through the screw channel 34. If the angle of one of the walls 35 is modified, the bone screw will sweep through a different angle from one side of the vertical axis to the other. In a specific embodiment, the angled walls 35 of the screw channel 34 are situated at 25 degrees from the vertical passing through the screw channel. Thus, in this specific embodiment, the bone screw can be oriented at infinitely variable angles between 25 degrees to the left and 25 degrees to the right of the vertical axis of the screw channel 34.

Figure 3A:
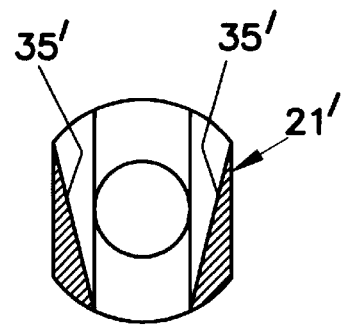
FIG. 3a is an end cross-sectional view of a connector body modified from the body in FIG. 3.

In an alternative embodiment, the screw channel 34 can be defined by angled walls 35 that meet at either the top or the bottom of the tapered body 21. In other words, the central vertices 36 are moved away from the center of the tapered body 21, such as the angled walls 35' depicted in the body 21' in FIG. 3a. In this instance, the center of pivot of the bone screw relative to the tapered body 21 will be altered. Commensurate changes in the angles of the angled walls 35 will determine the amount of angular deviation permitted between the bone screw and the connector assembly 20.

The tapered body 21 includes a generally cylindrical surface 38 at one end of the body adjacent the rod slot 25. The body also defines a tapered cylindrical or frusto-conical surface 39 extending from end 41 toward the cylindrical surface 38. In order to reduce the overall profile of the tapered body 21, the opposite sides of the body are flattened to define flat surfaces 40.

Figure 5:
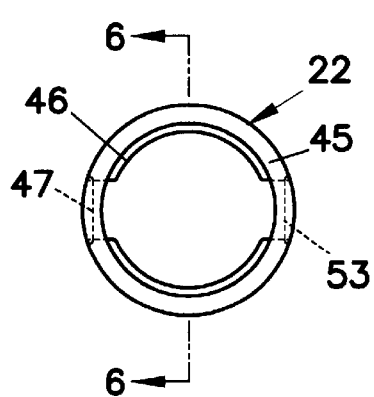
FIG. 5 is an end elevational view of the washer component of the connector assembly shown in FIG. 1.
Figure 6:
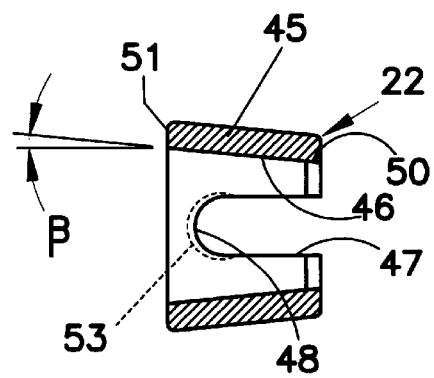
FIG. 6 is a side cross-sectional view of the washer shown in FIG. 5 taken along line 6—6 as viewed in the direction of the arrows.
Figure 7:
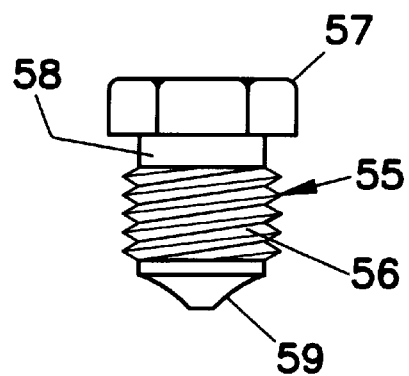
FIG. 7 is a side elevational view of a set screw used with the connector assembly shown in FIG. 1.

A further important component of the connector assembly 20 is the tapered washer 22. Details of the washer can be seen with reference to FIGS. 5 and 6. In accordance with the preferred embodiment, the tapered washer 22 is defined by a tapered cylindrical or frusto-conical wall 45. The wall defines a tapered inner surface 46 that is generally complementary to the tapered outer surface 39 of the tapered body 21. The tapered washer 22 is configured to fit over and around the tapered body 21, specifically at the tapered outer surface 39. The tapered inner surface 46 of the washer is circular so that the washer can be freely rotated about the tapered body 21.

The tapered washer 22 includes a screw slot 47 defined in diametrically opposed portions at one end of the washer. The end of each of the screw slots 47 defines a screw clamping surface 48 against which the bone screw shank 12 will bear when the connector assembly 29 is in its final tightened condition.

In accordance with the present invention, the tapered inner surface 46 increases in diameter from the first end 50 to the second end 52 of the washer. The taper angle of the inner surface 46 is at an angle β. In accordance with the invention, the angle of the tapered outer surface 39 of the tapered body 21 is an angle α. In one specific embodiment, these angles are substantially equal and are about 5.7 degrees. In accordance with the invention, the smallest diameter of the tapered inner surface 46, at first end 50 of the tapered washer 22, is slightly greater than the diameter of the non-tapered cylindrical surface 38 of the tapered body 21. Thus, the washer 22 can be easily loaded over the tapered body 21 with the second end 51 preceding the first end. In other words, when the tapered washer 22 is loaded onto the tapered body, the second end 51 will be positioned adjacent the end 41 of the tapered body 21. In this orientation, the screw slot 47 will be aligned over the screw channel 34 of the tapered body 21. A circular relief 53 can be defined adjacent the screw clamping surface 48 of each of the screw slots 47 to create a relatively sharp fixation edge for engaging the bone screw shank.

The inter-relationship between the tapered washer 22 and tapered body 21 provides an important feature of the connector assembly 20 of the present invention. Specifically, the smallest diameter of inner surface 46 at first end 50 of the tapered washer 22 is smaller than the largest diameter of the tapered outer surface 39 at end 41 of tapered body 21. Thus, as the washer 22 is translated along the length of the tapered body 21 toward end 41, the frictional engagement between the inner surface 46 and the outer surface 39 will gradually increase. In other words, the tapered inner surface 46 and tapered outer surface 39 can operate in the manner of a self-locking or self-holding taper to create a very strong and effective fixation between the washer 22 and the body 21. In accordance with a specific embodiment, this firm fixation will be achieved before the second end 51 of the washer 22 projects beyond the end 41 of the tapered body 21. This final frictional fixation between the washer and the body can be accomplished while the bone screw shank 12 is still slidably disposed within the elongated screw channel 34.

In the preferred embodiment, the complementary angles α and β of the inner and outer surfaces, respectively, are in the range of self-locking angles. This range of angles includes Morse tapers, American National Standard Self-Holding Tapers or Brown & Sharp tapers. In an alternative embodiment, steep tapers or self-releasing tapers, such as British Standard Tapers, can be utilized. With this taper, the washer can be easily released once the pressure from the pressure member is released.

The use of the complementary tapered inner and outer surfaces between the washer 22 and the body 21 provide a means for fixing the bone screw at its relative angle with respect to the connector assembly 20 and rod R, while still allowing the bone screw to translate within the screw channel 34. In this circumstance, the tapered washer 22 could simply be manually translated toward the end 41 of the tapered body 21 to achieve some type of frictional retention of the tapered washer on the body. However, in accordance with the present invention, a further loading and final fixation mechanism is contemplated. In particular, a set screw 55 is provided that is engaged within the threaded bore 27 of the tapered body 21. The set screw 55 includes a threaded body 56 with threads configured to engage the female threads of the bore 27. The set screw also includes driving head 57 for engagement by a driving tool. In one specific embodiment, the head 57 can be integrated to the threaded body 56 by way of a fracture initiation portion 58. In accordance with known technology, the driving head 57 of the set screw 55 can be severed from the threaded body 56 at the fracture initiation portion 58 once a pre-determined torque has been reached when applied to the driving head 57. This fracture initiation portion 58 provides the benefit of limiting the amount of torque that can be applied to the set screw 55 and thereby limiting the amount of load or pressure applied to the spinal rod R. In addition, removal of the driving head 57 reduces the prominence of the overall connector assembly construct 20.

The set screw 55 further includes an engagement tip 59, which in the illustrated embodiment is tapered to a blunt point. Other types of engagement tips 59 are contemplated, provided they permit application of a solid clamping force to a spinal rod within the connector assembly, while still allowing the rod to slide along the elongated rod slot 25 until the final clamping force is achieved.

Figure 9:
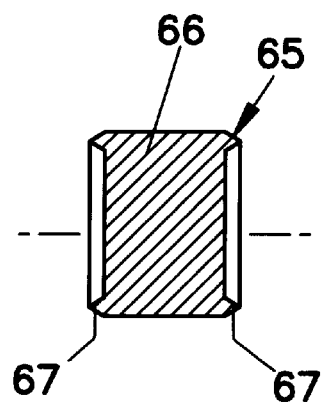
FIG. 9 is a side cross-sectional view of a transfer member for use with one embodiment of the connector assembly shown in FIG. 1.
Figure 10:
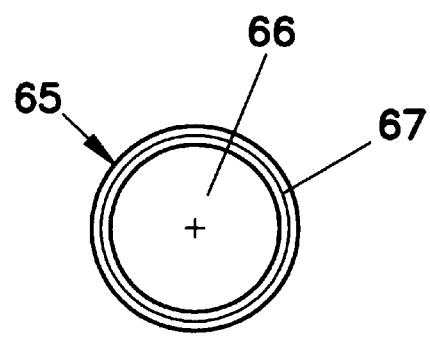
FIG. 10 is an end elevational view of the transfer member shown in FIG. 9.

An additional element of the connector assembly 20 is a transfer pin 65, as depicted in FIGS. 9 and 10. The transfer pin 65 includes cylindrical body 66 that is sized to be slidably received within the central bore 29. As discussed above, the cylindrical body 66 can include a threaded exterior so that it can be threaded through the threaded portion 30 of the central bore. In this manner, the transfer pin 65 can be preloaded into the tapered body 21 by threading the pin past the threaded portion 30. Once the transfer pin is fully within the central bore 29, it cannot be removed. In accordance with the preferred embodiment, the transfer pin 65 has a length that is greater than the distance between the window 31 of the central bore 29 and the intersection between the central bore 29 and the screw channel 34. Thus, the transfer pin 65 can be situated in the central bore 29 between the rod R and bone screw shank 12 and remain in contact with both components. In one specific embodiment, the transfer pin 67 can include annular ridges 65 at the opposite ends of the pin that can penetrate the surfaces of the other components. The annular ridges 67 can provide a clamping force and a higher degree of fixation when it bears against either the rod R or the shank 12 of the bone screw 10.

Figure 11:
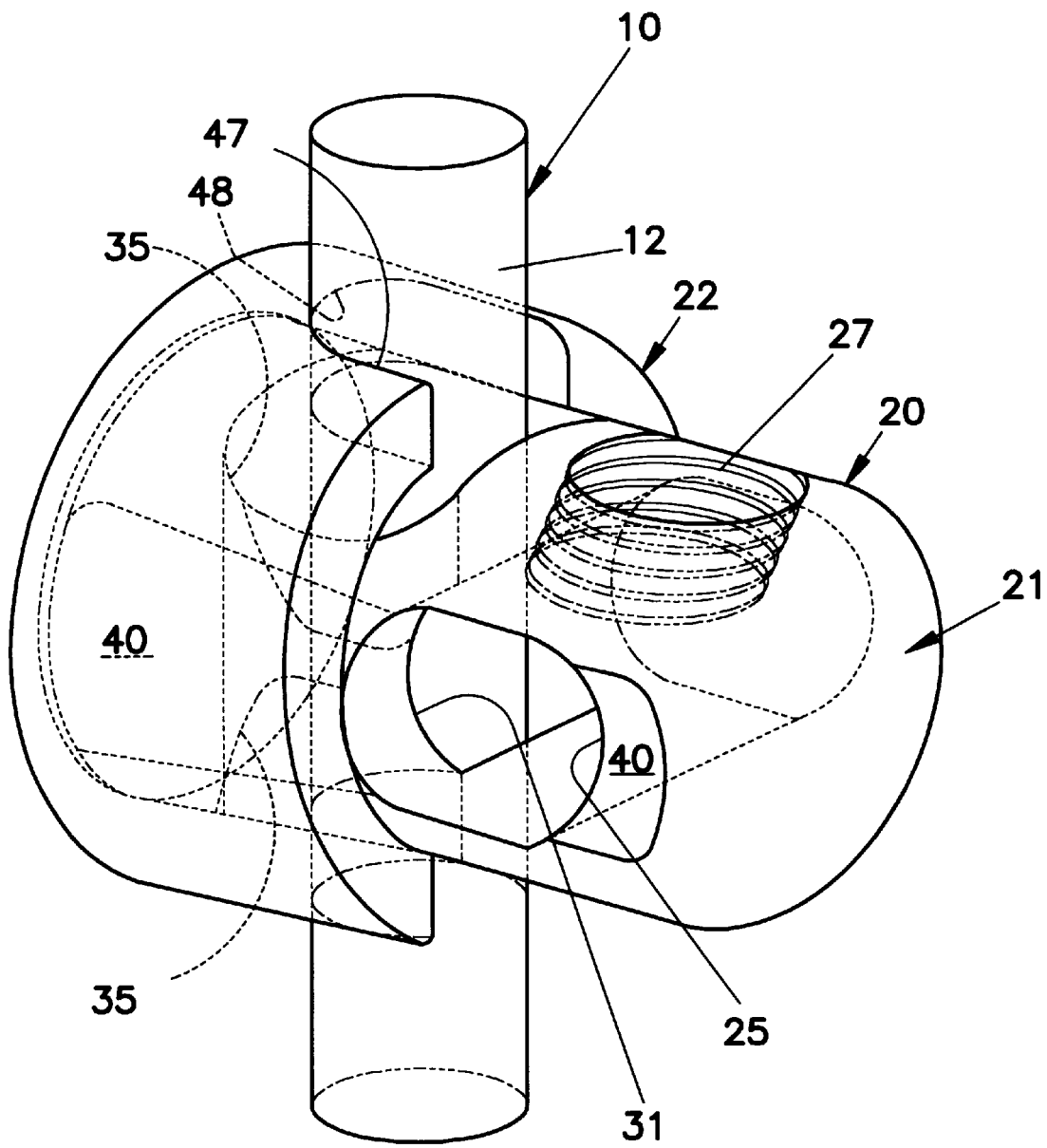
FIG. 11 is an enlarged perspective view of the connector body and washer engaged about a portion of a bone engaging fastener, with aspects of the connector assembly shown in phantom.
Figure 12:
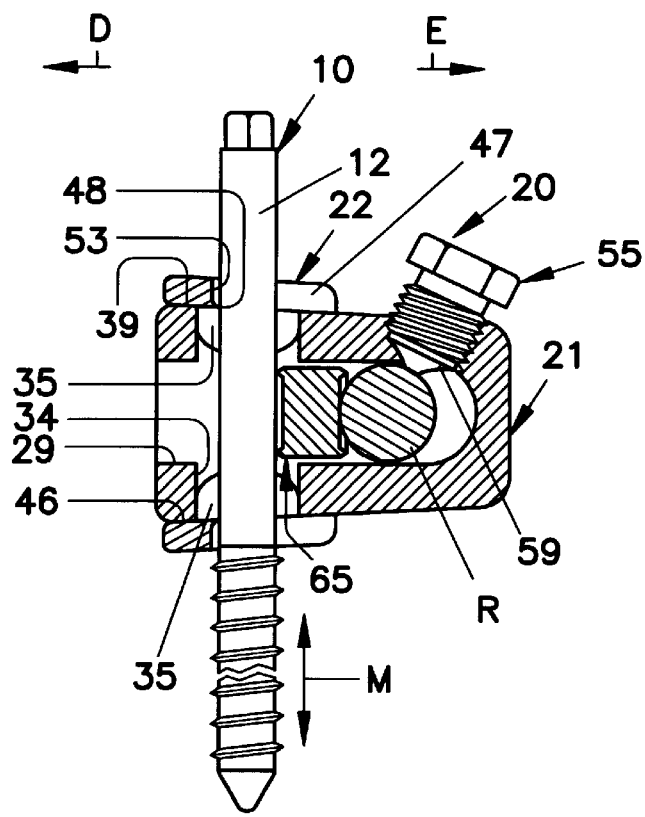
FIG. 12 is a side cross-sectional view of the connector assembly according to one embodiment of the invention.

Assembly of the various components of the connector assembly 20 is illustrated with respect to FIGS. 11 and 12. The connector assembly 20 is preferably provided to the surgeon with the transfer pin 65 loaded within the central bore 29, and with the tapered washer 22 disposed about the tapered body 21. Preferably, the tapered body 21 is staked at some portion of the cylindrical surface 38 adjacent the elongated rod slot 25 to keep the tapered washer 22 from sliding off of the tapered body 21. The set screw 55 can also be loosely threaded into the set screw bore 27 of the tapered body 21. The surgeon is thus provided with the entire connector assembly 20 that is ready to be engaged between the bone screw and rod.

Figure 13:
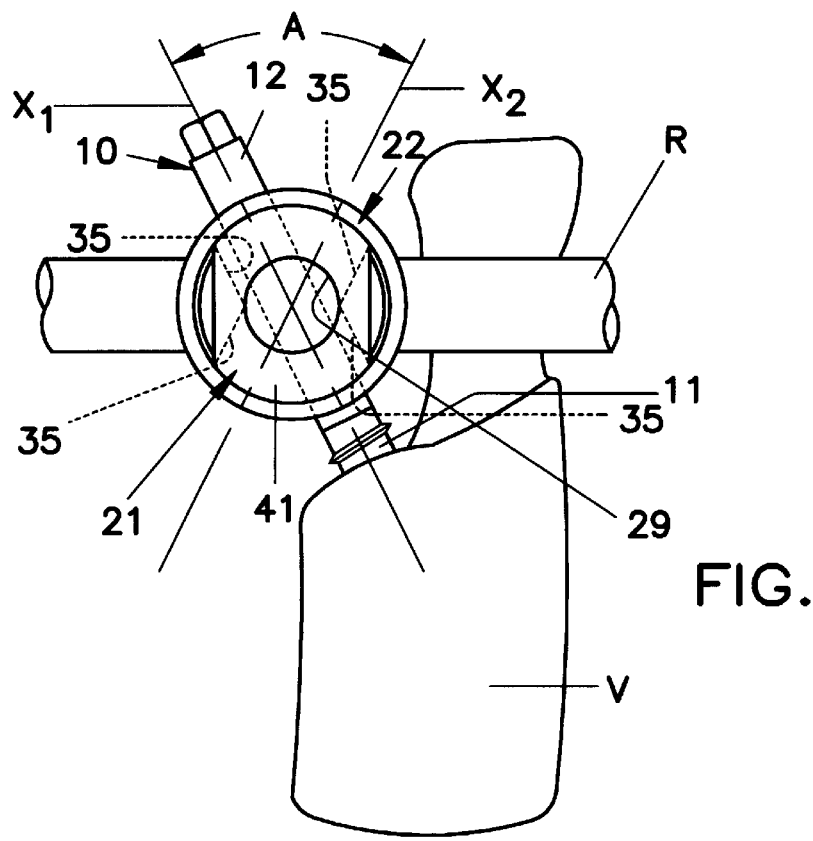
FIG. 13 is an end elevational view of the connector assembly shown in FIG. 12 engaged within the vertebrae of a human spine.

Since the illustrated embodiment includes a closed rod slot 25, the connector assembly 20 must be preloaded onto the spinal rod R (see FIG. 12). With the rod R loosely disposed within the rod slot 25, the connector assembly 20 is manipulated so that the smooth shank 12 of a bone screw 10 is oriented in line with the screw slot 47 of the tapered washer 22 and the screw channel 34 of the tapered body 21. It is understood that the bone screw 10 is already engaged within a vertebra of a patient, as depicted in FIG. 13. Thus, the manipulation must be of the connector assembly 20 and rod R, and not of the bone screw 10. In some prior fixation systems, the surgeon was required to not only manipulate the implants, but also the vertebra itself in order to engage and connect the various components of the implant. The present invention eliminates this "fiddle factor".

Since the washer 22 is at first loosely disposed about the tapered body 21, it is free to rotate to meet the particular orientation of the smooth shank 12 of the bone screw 10. When the screw slot 47 of the washer 22 is aligned with the shank, the tapered body 21 can also be manipulated so that the shank can be readily extended through the through channel 34, projecting upward through the tapered body 21 and through the opposite screw slot 47 of the tapered washer 22. At this point, the connector assembly 20 and the spinal rod R can be lowered to their final position within the patient. As the assembly 20 is lowered, the washer 22 and screw channel 34 of the tapered body 21 slide along the smooth shank 12.

It is understood that at any point after the shank 12 of the bone screw 10 has been extended through the connector assembly 20, the tapered washer 22 can be locked onto the tapered body 21 to fix the angular orientation of the bone screw 10 relative to the spinal rod R. This locking can be accomplished by manually driving the tapered washer 22 in the direction of the arrow D in FIG. 12.

Preferably, however, the tapered washer 22 is moved to its final clamping position by operation of the pressure member or set screw 55. As the set screw 55 is advanced into the threaded bore 27, it bears against and exerts pressure on the spinal rod R captured within the rod slot 25. Increasing threading of the set screw 55 gradually pushes the rod R toward the opposite end of the rod slot 25. At this point, the rod contacts the transfer pin 65 and gradually pushes the pin along the central bore 29 toward the end 41 of the tapered body 21. As the transfer pin 65 translates along the central bore 29, it contacts the shank 12 of the bone screw 10. Since the bone screw is held stationary by the patient's spine, the shank 12 will not translate when pressure is exerted on it by the transfer pin 65. Instead, the reaction force caused by pressure of the pin 65 against the shank 12 will cause the tapered body 21 to shift in the direction of arrow E opposite to the arrow D in FIG. 12. When this occurs, the tapered washer 22 is drawn toward the shank 12 until the screw clamping surface 48 contacts the shank.

As the tapered body 21 moves further in the direction of the arrow E, the tapered outer surface 39 of the body 21 passes deeper into the tapered inner surface 46 of the washer 22. During this process, the frictional force between the two tapered surfaces of the body 21 and washer 22 reaches a point where the washer will no longer slide over the outer tapered surface 39 of the body. At that point, continued tightening of the set screw 55 will cause the driving head 57 to sever at the fracture initiation portion 58. In that orientation, as depicted in FIG. 12, the entire connector assembly 20 is tightly locked and clamped against both the bone screw 10 and the spinal rod R. In the preferred embodiment, the tapered body and tapered washer are at self-locking angles. In this instance, the washer will remain tightly clamped to the body even if the set screw is loosened. In embodiments utilizing a steep taper, the self-releasing feature will allow the washer to be easily displaced when the set screw is loosened.

It should be appreciated that the connector assembly 20 of the present invention permits relative movement between the bone screw 10 and the spinal rod R in multiple degrees of freedom. First, as with most prior clamping devices, the connector assembly 20 itself can be rotated around the spinal rod R about the longitudinal axis of the rod. The present invention provides additional degrees of freedom, first in that the position of the connector assembly 20 along the length L (see FIG. 8) of the shank can be varied in the direction of the arrows M in FIG. 12. Finally, as shown in FIG. 13, the relative angle between the bone screw 10 and the spinal rod R can be varied. For example, the axis $X_1$ of the bone screw 10 can be non-perpendicular with respect to the spinal rod. The connector assembly 20 can also be manipulated to accommodate a bone screw in which its axis $X_2$ is aligned at an angle A from the position of the axis $X_1$,. As indicated above, in one specific embodiment, this relative angle range A can be 50 degrees. The relative height or axial location variation in the direction of the arrows M depends upon the length L of the shank 12 of the bone screw. In one specific embodiment, that length is about 30 mm. In one embodiment of the connector assembly, the body has an outer diameter of a little over 11 mm. Thus, movement in the direction of the arrows M can range between 0 and 19 mm. In accordance with a preferred technique using the connector assembly 20 of the present invention, the excess portion of the shank 12 that projects outward from the connector assembly 20 can be severed at the tapered washer 22 to reduce the overall prominence of the construct.

Figure 14:
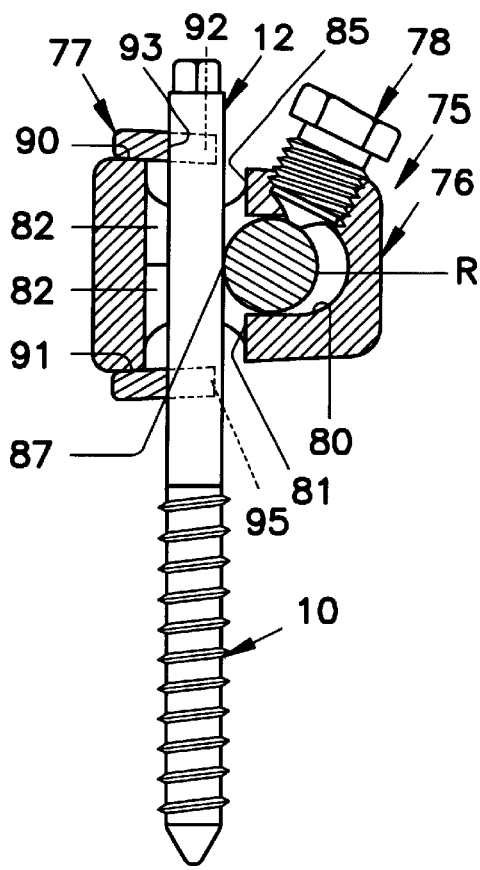
FIG. 14 is a side cross-sectional view of an alternative embodiment of the connector assembly according to the present invention.

A further embodiment of the present invention is depicted in cross-section in FIG. 14. In this embodiment, a connector assembly 75 provides direct contact between the bone screw 10 and the spinal rod R. The connector assembly 75 includes a tapered body 76, a tapered washer 77 and a set screw 78 that are similar to the like components in the previous embodiment. However, the tapered body 76 is modified so that the elongated rod slot 80 directly intersects the screw slot 81. As can be seen in FIG. 14, this intersection between the two slots allows for direct contact between the shank 12 of the bone screw 10 and the spinal rod R when the rod is under pressure from the set screw 78. The screw channel 81 can be configured just like the screw channel 34 in the previous embodiment, namely to include sets of angled walls 82. The interface between the rod slot 80 and screw channel 81 occurs at a slot window. In the previous embodiment, a central bore 29 was provided. This central bore is not utilized in the connector assembly 75, which reduces the overall length of the assembly. Since the bore is eliminated, the transfer pin 65 is also eliminated.

The tapered washer 77 includes a tapered inner surface 91 that corresponds to a tapered outer surface 90 of the body 76. These two tapered or frusto-conical surfaces operate the same as the like surfaces described with respect to the previous embodiment. The tapered washer 77 likewise includes a screw slot 92 that is configured to receive the smooth shank 12 of the bone screw 10. The screw slot terminates inboard in a screw clamping surface 93 which bears against the shank 12 of the bone screw when the connector assembly 75 is in its final tightened position. As depicted in FIG. 14, the tapered washer 77 is sized so that its end 95 does not project beyond the diameter of the bone screw 10. Put in other terms, the screw slot 92 of the tapered washer 77 has a length that is less than the outer diameter of the bone screw. In this manner, the washer cannot contact the spinal rod R. Alternatively, a second slot can be provided that is offset from screw slot 92 to receive the rod R therein.

With this embodiment, the connector assembly 75 relies upon the screw-rod interface 87 for effectively clamping the components together. Again, the set screw 78 provides the primary pressure force to drive all of the components into engagement. Since a transfer pin is not used, the contact between the rod and screw is essentially at a single point 87. Various surface treatment can be applied to either or both of the shank 12 and the spinal rod R to enhance the degree of fixation between the components.

One obvious difference between the connector assembly 75 and the connector assembly 20 is the lack of the transfer pin 65. Another difference is that the connector assembly 75 requires that the spinal rod R be affixed directly adjacent the bone screw 10. In some instances, variable lateral displacement of the two components is necessary. In this instance the connector assembly 20 is used since there is no direct contact between the bone screw 10 and rod R. It is understood that the amount of lateral offset between the two components can be varied by changing the overall length of the tapered body 21, the length of the central bore 28 and the length of the transfer pin 65.

In each of the illustrated embodiments, both the rod slot 25, 80 and the screw channel 34, 81 are closed. In other words, the respective rod R or screw 10 must be essentially threaded through the respective slot or channel. The present invention contemplates modifications to the tapered body 21, for example, that allows for open loading. In other words, the rod slot 25 formed in the tapered body 21 could be extended through to the end of the tapered body 21. In this instance, the connector assembly 20 can be engaged to a spinal rod R that is already within the patient. The set screw 55 would then not only provide the clamping force for final tightening of the assembly 20, it would also provide a mechanism for loosely retaining the spinal rod R within the modified rod slot, when the set screw was tightened part way into the rod slot 25. Similar modifications can be made to accommodate side-loading of the bone screw 10 into both the tapered body and the tapered washer.

Figure 15:
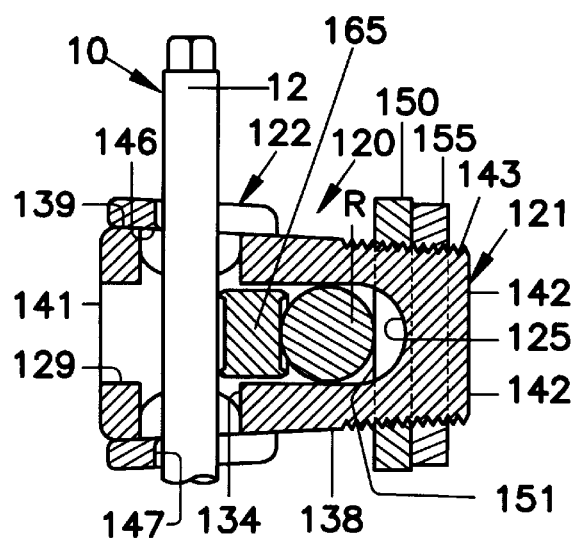
FIG. 15 is a side cross-sectional view of another embodiment of the connector assembly according to the present invention.

In a further embodiment depicted in FIG. 15, a connector assembly 120 utilizes a pressure member other than the set screw 55 shown in FIG. 12. In particular, the connector assembly 120 includes a tapered body 121 and a tapered washer 122. The body defines an elongated rod slot 125, a central bore 129 and a screw channel 134 that are substantially similar to the like named components in the previous embodiment. The tapered body 121 includes a cylindrical surface 138 and a tapered outer surface 139 that mates with a tapered inner surface 146 of the tapered washer 122. The tapered washer 122 includes a screw slot 147, all in accordance with the prior embodiment. As with the prior embodiment, the connector assembly 120 of the embodiment of FIG. 15 provides a transfer member 165 between the rod R and the shank 12 of the bone screw 10. As with the embodiment of FIG. 12, the tapered body 121, and particularly the tapered outer surface 139 increases in diameter toward end 141.

In a modification from the previous embodiment, the set screw is replaced by a threaded portion 143 extending from end 142 of the tapered body 121. The threaded portion 143 preferably overlaps a portion of the rod channel 125. The threads of the threaded portion 143 are configured to mate with internal threads of a machine nut 155. Interposed between the nut 155 and the rod R is a washer 150 that slides over the threaded portion 143 of the tapered body 121. The washer 150 contacts the rod R at surface 151.

In this embodiment, the nut 155 is progressively tightened onto the threaded portion 143 of the tapered body 121. As the nut 155 is advanced, it pushes the washer 150 against the rod R, which operates against the transfer member 65. The remaining effects on the screw 10 and the tapered washer 122 are as described previously. Thus, this embodiment retains the effects of the corresponding mating tapers between the tapered washer 122 and the tapered body 121 of the prior embodiment. However, the pressure member is now the machine nut 155 and washer 150, instead of the set screw 55.

Figure 16:
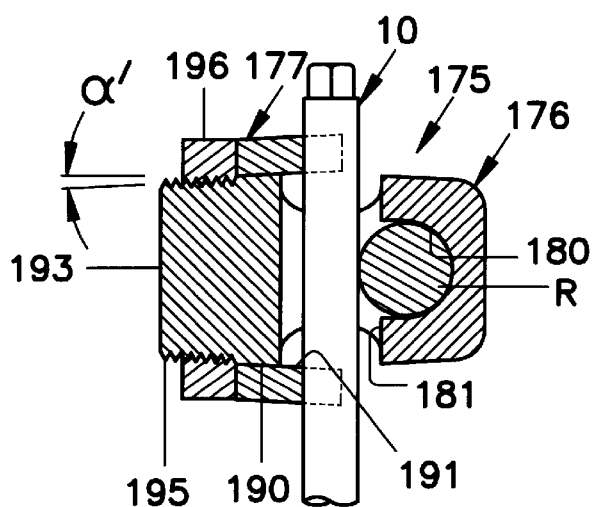
FIG. 16 is a side cross-sectional view of a further embodiment of the connector assembly according to the present invention.

In yet a further embodiment, a connector assembly 175 is depicted in FIG. 16. The connector assembly includes a tapered body 176 and a tapered washer 177. In this embodiment, the body 176 defines a rod slot 180 and a screw channel 181. In the depicted embodiment, the rod slot 180 and screw channel 181 intersect, although the interface between the bone screw 10 and the spinal rod R can be by way of a transfer member, such as transfer member 65.

In accordance with this embodiment, the tapered body 176 is tapered from end 193, which is adjacent the screw channel 181. In other words, the taper of the tapered body 176 is at the opposite end of the body from the body 21 or 121 of the prior embodiments. In this embodiment, the tapered outer surface 190 of the body 176 increases in diameter from end 193 toward the screw channel 181. This requires a commensurate change in the angle of the tapered inner surface 191 of the tapered washer 177. The relative taper angles between the inner surface 191 and the outer surface 190 can be similar to the relative taper angles in the previous embodiments. Specifically, the angle $\alpha'$ of the tapered outer surface 190 can be 5.7 degrees, as in the prior specific embodiment, except that the taper increases from the end 193.

In a further aspect of the this embodiment, the portion of the body 176 extending from end 193 includes external threads 195. These threads mate with a correspondingly internally threaded nut 196. In the specific illustrated embodiment, the nut 196 and external threads 195 can also be tapered to provide a self-locking feature. Alternatively, the threaded portion of the tapered body 176 can be non-tapered, together with the nut 196. In this instance, a washer, such as washer 150, can be interposed between the nut 196 and the tapered washer 177.

In the operation of the connector assembly 175 shown in FIG. 16, tightening of the nut 196 onto the threads 195 causes a force to operate on the tapered washer 177. As the washer is pushed toward the rod R, it pushes against the bone screw 10 and ultimately applies a pressure force against the rod R until the rod is lodged within the rod channel 180.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A connector for connecting a bone engaging fastener to a longitudinal member, the fastener having an elongated shank, said connector comprising:

a body defining a first channel configured for receiving a portion of the longitudinal member therethrough and a second channel adjacent said first channel configured for receiving the elongated shank of the fastener therethrough, said second channel intersecting said first channel to define a window therebetween to permit contact between said portion of the longitudinal member and the elongated shank of the fastener, said body including an outer surface intersected by said second channel;

a washer slidably disposed on said outer surface of said body, said washer having a first end and an opposite second end and defining a slot at said first end, said slot configured to receive the elongated shank of the fastener therethrough, said slot having a clamping surface; and a pressure member mounted on the body and contacting said portion of the longitudinal member when said shank is received within said slot of said washer, said pressure member being operable to push said longitudinal member toward said slot and thereby push said shank against said clamping surface of said slot of said washer.

2. The connector assembly according to claim 1, further comprising means for retaining said washer on said member upon operation of said pressure member.

3. The connector assembly according to claim 2, wherein said means for retaining includes a tapered outer surface defined on said body and a complementary tapered inner surface on said washer.

4. The connector assembly according to claim 3, wherein said tapered outer surface and said tapered inner surface define a self-locking taper.

5. The connector assembly according to claim 3, wherein said tapered outer surface and said tapered inner surface define a self-releasing taper.

6. The connector assembly according to claim 1, wherein said slot in said washer has a length from said clamping surface that is less than the transverse dimension of said one element.

7. The connector assembly according to claim 1, wherein said first channel is elongated in a direction toward said second channel.

8. The connector assembly according to claim 1, wherein said second channel is elongated in a direction toward said first channel.

9. The connector assembly according to claim 1, wherein:
said pressure member is a set screw; and
said body defines a threaded bore intersecting said first channel.

10. The connector assembly according to claim 9, wherein said threaded bore is arranged at a non-colinear angle relative to a line between said first channel and said second channel.

11. The connector assembly according to claim 1, wherein:
said pressure member is an internally threaded nut; and
said body includes an externally threaded portion adjacent the other of said first channel and said second channel, said externally threaded portion mating with said internally threaded nut.

12. The connector assembly according to claim 11, further comprising a washer disposed about said body between said pressure member and said longitudinal member.

13. The connector assembly according to claim 1, wherein said first channel is a closed channel so that tht longitudinal member must be threaded into said channel.

14. A connector for connecting a bone engaging fastener to a longitudinal member, the fastener having an elongated shank, said connector comprising:

a body defining a first channel configured for receiving a portion of the longitudinal member therethrough, a second channel adjacent said first channel configured for receiving the elongated shank of the fastener therethrough and a third channel communicating between said first channel and said second channel, said body including an outer surface intersected by said second channel;

a transfer member slidably disposed within said third channel and configured to simultaneously contact the elongated shank of the fastener and the portion of the longitudinal member when disposed within said third channel;

a washer defining an inner surface substantially complementary with said outer surface of said body, said washer having a first end and an opposite second end and defining a slot at said first end, said slot configured to receive the elongated shank of the fastener and the portion of the longitudinal member therethrough, said slot having a clamping surface, said washer being slidably disposed on said outer surface of said body;

a pressure member mounted on the body and contacting said portion of the longitudinal member when said shank is received within said slot of said washer, said pressure member being operable to push said longitudinal member against said transfer member, and said transfer member against said shank, and thereby push said shank against said clamping surface of said slot of said washer; and means for retaining said washer on said member upon operation of said pressure member.

15. The connector assembly according to claim 14, further comprising means for retaining said washer on said member upon operation of said pressure member.

16. The connector assembly according to claim 15, wherein said means for retaining includes a tapered outer surface defined on said body and a complementary tapered inner surface on said washer.

17. The connector assembly according to claim 16, wherein said tapered outer surface and said tapered inner surface define a self-locking taper.

18. The connector assembly according to claim 16, wherein said tapered outer surface and said tapered inner surface define a self-releasing taper.

19. The connector assembly according to claim 14, wherein said slot in said washer has a length from said clamping surface that is less than the transverse dimension of said shank.

20. The connector assembly according to claim 14, wherein said first channel is elongated in a direction toward said second channel.

21. The connector assembly according to claim 14, wherein said second channel is elongated in a direction toward said first channel.

22. The connector assembly according to claim 14, wherein:

said pressure member is a set screw; and said body defines a threaded bore intersecting the other of said first channel and said second channel.

23. The connector assembly according to claim 22, wherein said threaded bore is arranged at a non-colinear angle relative to a line between said first channel and said second channel.

24. The connector assembly according to claim 14, wherein:

said pressure member includes an internally threaded nut; and said body includes an externally threaded portion adjacent said first channel, said externally threaded portion mating with said internally threaded nut.

25. The connector assembly according to claim 24, wherein the pressure member includes a washer disposed about said body between said nut and said portion of the longitudinal member.

26. The connector assembly according to claim 14, wherein said first channel is a closed channel so that tht longitudinal member must be threaded into said channel.

27. A connector for connecting a bone engaging fastener to a longitudinal member, the fastener having an elongated shank said connector comprising:

a body defining a first channel configured for receiving a portion of the longitudinal member therethrough and a second channel adjacent said first channel configured for receiving the elongated shank of the fastener therethrough, said body including an outer surface intersected by said second channel, said second channel having at least one portion that is tapered toward said outer surface to permit variable angular orientations of the elongated shank and the portion of the longitudinal member when said shank is received within said second channel;

a washer defining an inner surface facing said outer surface of said body when said washer is rotatably disposed on said outer surface, said washer having a first end and an opposite second end and defining a slot at said first end, said slot configured to receive said shank therethrough; and means between said outer surface of said body and said inner surface of said washer for fixing said washer against rotation about said outer surface.

28. The connector asssembly according to claim 27, wherein said one channel includes an upper portion that is tapered outwardly to said outer surface and an opposite lower portion that is tapered outwardly to said outer surface.

29. The connector assembly according to claim 28, wherein said means for fixing includes complementary tapered surfaces.

30. A connector for connecting a bone engaging fastener to a longitudinal member, the fastener having an elongated shank, said connector comprising:

a body defining a first channel configured for receiving a portion of the longitudinal member therethrough and a second channel adjacent said first channel configured for receiving the elongated shank of the fastener therethrough, said body including an outer surface intersected by said second channel, said outer surface being tapered from said second channel toward said first channel, said second channel having a longitudinal axis and being configured to permit movement transverse to said longitudinal axis, of the elongated shank and the portion of the longitudinal member when said shank is received within said second channel; and a washer having a first end and an opposite second end and defining a slot at said first end configured to receive said shank therethrough, and further defining an inner surface that is tapered from said first end to said second end complementary to said tapered outer surface, said washer being slidably disposed on said body for increasing frictional engagement between said tapered inner surface and said tapered outer surface.

\* \* \* \* \*

UNITED STATES PATENT AND TRADEMARK OFFICE
CERTIFICATE OF CORRECTION

PATENT NO. : 5,947,967
DATED : September 7, 1999
INVENTOR(S) : B. Thomas Barker

It is certified that error appears in the above-identified patent and that said Letters Patent is hereby corrected as shown below:

Title Page,
Column 1, under [56] References Cited, add:
-- 5,534,002  06/1996  Brumfield et al.
   5,209,752  05/1993  Ashman et al.
   5,176,680  01/1993  Vignaud et al.
   5,102,412  04/1992  Rogozinski --.

Signed and Sealed this

Twenty-fifth Day of September, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,947,967  
DATED : September 7, 1999  
INVENTOR(S) : B. Thomas Baker Page 1 of 1

It is certified that error appears in the above-identified patent and that said Letters Patent is hereby corrected as shown below:

Title page,
Item [73], Assignee: change "SDGT" to -- SDGI --.

Signed and Sealed this

Fifth Day of February, 2002

Attest:

JAMES E. ROGAN  
*Director of the United States Patent and Trademark Office*

*Attesting Officer*